US012617873B2

(12) United States Patent
Zurbriggen

(10) Patent No.: US 12,617,873 B2
(45) Date of Patent: May 5, 2026

(54) METHOD OF PURIFYING POLYSACCHARIDES

(71) Applicant: LONZA LTD, Visp (CH)

(72) Inventor: Andreas Zurbriggen, Visp (CH)

(73) Assignee: LONZA LTD, Visp (CH)

( * ) Notice: Subject to any disclaimer, the term of this patent is extended or adjusted under 35 U.S.C. 154(b) by 873 days.

(21) Appl. No.: 17/756,282

(22) PCT Filed: Nov. 30, 2020

(86) PCT No.: PCT/US2020/062586
§ 371 (c)(1),
(2) Date: May 20, 2022

(87) PCT Pub. No.: WO2021/108792
PCT Pub. Date: Jun. 3, 2021

(65) Prior Publication Data
US 2022/0411540 A1      Dec. 29, 2022

Related U.S. Application Data

(60) Provisional application No. 62/941,941, filed on Nov. 29, 2019.

(51) Int. Cl.
| | |
|---|---|
| *C08B 37/00* | (2006.01) |
| *A61K 31/722* | (2006.01) |
| *A61K 35/74* | (2015.01) |
| *A61K 36/06* | (2006.01) |
| *A61K 39/00* | (2006.01) |
| *A61K 39/09* | (2006.01) |
| *A61K 47/64* | (2017.01) |

(52) U.S. Cl.
CPC ........ *C08B 37/0003* (2013.01); *A61K 31/722* (2013.01); *A61K 35/74* (2013.01); *A61K 36/06* (2013.01); *A61K 39/0002* (2013.01); *A61K 39/092* (2013.01); *A61K 47/64* (2017.08)

(58) Field of Classification Search
CPC .. C08B 37/0003; A61K 31/722; A61K 35/74; A61K 36/06; A61K 39/0002; A61K 39/092; A61K 47/64
See application file for complete search history.

(56) References Cited

U.S. PATENT DOCUMENTS

| | | | |
|---|---|---|---|
| 4,242,501 A | 12/1980 | Cano et al. | |
| 5,714,354 A | 2/1998 | Arnold et al. | |
| 2007/0141084 A1 | 6/2007 | Lee et al. | |
| 2017/0157241 A1 * | 6/2017 | Li ........................... A61K 39/39 |

FOREIGN PATENT DOCUMENTS

| | | | | |
|---|---|---|---|---|
| CA | 2884241 A1 * | 3/2014 | ........... | A61K 39/092 |
| CN | 101180079 A | 5/2008 | | |

| | | | | |
|---|---|---|---|---|
| CN | 102653565 A | 9/2012 | | |
| CN | 103695500 A | 4/2014 | | |
| JP | S56-29524 A | 3/1981 | | |
| JP | 2018-514624 A | 6/2018 | | |
| KR | 102028693 B1 * | 10/2019 | ............. | B01D 15/08 |
| WO | 2011/148382 A1 | 12/2011 | | |
| WO | 2016/174683 A1 | 11/2016 | | |
| WO | 2018/203268 A1 | 11/2018 | | |

OTHER PUBLICATIONS

Morais, Victor, Valerie Dee, and Norma Suárez. "Purification of capsular polysaccharides of *Streptococcus pneumoniae*: traditional and new methods." Frontiers in Bioengineering and Biotechnology 6 (2018): 145. (Year: 2018).*
CTAB product information from Riverland Trading website. Obtained from <www.riverlandtrading.com> on Sep. 17, 2025 (Year: 2025).*
Barahona et al., "Bioactive polysaccharides from marine algae," *Bioactive Carbohydrates and Dietary Fibre* 4(2):125-138 (2014).
Guo et al., "Polysaccharides: Structure and Solubility," *Solubility of Polysaccharides* 2:8-21 (2017).
Guo, Z. and Jennings, H. 2001 "Protein-polysaccharide conjugation" In *Methods in Molecular Medicine, Meningococcal Vaccines. Methods and Protocols*, Eds. Pollard, A.J. and Maiden, M.C.J., Humana Press Inc., Totowa, N.J. 66: pp. 49-54.
Lynch et al., "Lactic acid bacteria exopolysaccharides in foods and beverages: Isolation, properties, characterization, and health benefits," *Ann Rev Food Sci Technol* 9:155-176 (2018).
Snarr et al., "Immune Recognition of Fungal Polysaccharides," *Journal of Fungi* 3(3):47 (2017).
Turner et al., "Novel polysaccharide-protein conjugates provide an immunogenic 13-valent pneumococcal conjugate vaccine for *S. pneumoniae*," *Syn Sys Biol* 2(1): 49-58 (2017).
Xu et al., "Recent Advances in Marine Algae Polysaccharides: Isolation, Structure, and Activities," *Marine Drugs* 15(12):388, 2017.
International Search Report and Written Opinion issued in PCT/US2020/062586, dated Feb. 18, 2021.
Kothari et al., "A novel method for purification of Vi capsular polysaccharide produced by *Salmonella enterica* subspecies *enterica serovar Typhi*," Vaccine 31 (42):4714-4719 (2013).

* cited by examiner

*Primary Examiner* — Scarlett Y Goon
*Assistant Examiner* — David H Cho
(74) *Attorney, Agent, or Firm* — Medler Ferro Woodhouse & Mills PLLC

(57) ABSTRACT

The present disclosure provides a method of purifying polysaccharides from a cell lysate, comprising partially purifying the cell lysate comprising an impurity and a polysaccharide to obtain a clarified crude lysate; mixing the clarified crude lysate with a neutralization solution comprising a salt to form a neutralized lysate; mixing the neutralized lysate with a precipitation solution comprising cetyltrimethylammonium bromide to form a first supernatant and a first precipitate; and separating the first precipitate from the first supernatant, wherein the polysaccharide is located in the first supernatant. The present disclosure further provides a method of making a polysaccharide vaccine. Also provided are vaccines, delivery systems, compositions and polysaccharides made by the methods described herein.

22 Claims, No Drawings

METHOD OF PURIFYING POLYSACCHARIDES

FIELD OF THE INVENTION

The present disclosure provides a method of purifying polysaccharides from a cell and/or cell lysate. The present disclosure further provides a method of making a polysaccharide vaccine. Also provided are vaccines, delivery systems, compositions, and polysaccharides made by the methods described herein.

BACKGROUND

Pathogenic bacteria often have a cell surface capsule coated with polysaccharides. In a similar manner, pathogenic fungi can have a cell wall containing polysaccharides. Upon infection, these bacterial and fungal polysaccharides interfere with the immune response by preventing host antibodies from attaching to the cells. These polysaccharides have been discovered to be effective vaccines against the bacterial or fungal pathogens. In certain instances, multiple polysaccharides are conjugated into one vaccine formulation to increase protection against multiple serotypes or strains, and/or to improve the effectiveness of the vaccine. Additionally, polysaccharides have been used as non-antigen specific vaccine adjuvants to enhance the immunogenicity of vaccines.

Polysaccharides used in vaccine formulations can be isolated from the bacteria or fungi after culturing the organism, then lysing and purifying the polysaccharides from undesired impurities. Typical impurities can include cellular proteins, nucleic acids, other cellular components, and components of the culture medium. In general, polysaccharides can be charged, e.g., positively charged or negatively charged, or neutral. Separation of each type of polysaccharide from impurities may require different processes, e.g., different reagents and concentrations, separation procedure, etc. For example, U.S. Pat. No. 5,714,354 utilizes two separate processes for the purification of negatively charged polysaccharides and neutral polysaccharides, each purification process being a multi-day procedure that involves several sub-processes. Furthermore, the use of different reagents in each of the separate purification procedures can lead to reduced consistency in yield and quality. Moreover, use of different processes can increase burden for manufacture compliance, since each step and reagent may need to be evaluated separately during process characterization, resulting in lower efficiency and higher costs. Thus, purification of polysaccharides often can be a cumbersome, complex, time consuming, and inefficient endeavor.

SUMMARY OF THE INVENTION

In some embodiments, the disclosure provides a method of purifying polysaccharides from a cell lysate, the method comprising (a) partially purifying the cell lysate comprising a polysaccharide and an impurity to obtain a clarified crude lysate; (b) mixing the clarified crude lysate with a neutralization solution comprising about 100 mM to about 2 M salt to form a neutralized lysate; (c) mixing the neutralized lysate with a precipitation solution comprising about 0.1% v/v to about 6% v/v cetyltrimethylammonium bromide (CTAB) to form a first supernatant and a first precipitate; and (d) separating the first precipitate from the first supernatant, wherein the polysaccharide is substantially located in the first supernatant.

In some embodiments, the partially purifying the cell lysate comprises precipitation, centrifugation, filtration, or combination thereof. In some embodiments, the filtration comprises depth filtration, tangential flow filtration (TFF), sterile filtration, or combination thereof In some embodiments, the neutralization solution comprises about 200 mM to about 1 M salt. In some embodiments, the neutralization solution comprises about 250 mM to about 650 mM salt. In some embodiments, the neutralization solution comprises about 300 mM to about 500 mM salt. In some embodiments, the salt is NaCl, KCl, CH$_4$Cl, NH$_4$Cl, MgCl$_2$, CaCl$_2$, Na$_3$PO$_4$, or combination thereof. In some embodiments, the neutralization solution comprises about 440 mM NaCl.

In some embodiments, the mixing of the clarified crude lysate with the neutralization solution in (b) is performed simultaneously with or prior to a filtration step, wherein the filtration step is prior to (c). In some embodiments, the mixing in (b) is performed simultaneously with the filtration step. In some embodiments, the filtration comprises tangential flow filtration (TFF).

In some embodiments, the precipitation solution comprises about 0.1% v/v to about 10% v/v CTAB. In some embodiments, the precipitation solution comprises about 0.2% v/v to about 5% v/v CTAB. In some embodiments, the precipitation solution comprises about 0.5% v/v to about 4% v/v CTAB. In some embodiments, the precipitation solution comprises about 1% v/v to about 3% v/v CTAB.

In some embodiments, the cell lysate comprises a positively charged polysaccharide, a neutral polysaccharide, a negatively charged polysaccharide, or combination thereof. In some embodiments, the positively charged polysaccharide, the neutral polysaccharide, the negatively charged polysaccharide, or combination thereof are substantially in the first supernatant.

In some embodiments, the impurity is substantially in the first precipitate. In some embodiments, the impurity comprises a polynucleotide. In some embodiments, the polynucleotide is DNA, RNA, or combination thereof.

In some embodiments, the mixing in (b), (c), or both, is performed by shaking, stirring, or pumping. In some embodiments, the separating is performed by centrifugation, filtration, or combination thereof In some embodiments, the method further comprises subjecting the first supernatant to ultrafiltration, diafiltration, or combination thereof to produce a retentate and a permeate, wherein the polysaccharide is substantially in the retentate, and the CTAB is substantially in the permeate. In some embodiments, the ultrafiltration, diafiltration, or combination thereof is tangential flow filtration (TFF).

In some embodiments, the method further comprises subjecting the retentate to carbon filtration. In some embodiments, the method further comprises subjecting the retentate to chromatography.

In some embodiments, the method further comprises adding potassium iodide (KI) to the first supernatant to form a second precipitate and a second supernatant, wherein the polysaccharide is substantially in the second supernatant and the CTAB is substantially in the second precipitate. In some embodiments, the method does not comprise a chromatography step prior to the addition of KI.

In some embodiments, the method further comprises separating the second supernatant from the second precipitate by centrifugation, filtration, or combination thereof. In some embodiments, the method further comprises subjecting the second supernatant to carbon filtration. In some embodiments, the method further comprises subjecting the second supernatant to chromatography.

In some embodiments, chromatography comprises ceramic hydroxyapatite type (CHT) chromatography, hydrophobic interaction chromatography (HIC), or combination thereof. In some embodiments, the chromatography comprises CHT chromatography and HIC. In some embodiments, the HIC is performed using a chromatography column or membrane comprising phenyl groups.

In some embodiments, the method further comprises ultrafiltration, diafiltration, or combination thereof following the chromatography, to concentrate the polysaccharide. In some embodiments, the ultrafiltration, diafiltration, or combination thereof is tangential flow filtration.

In some embodiments, the method does not comprise a first precipitate containing greater than 10% of the polysaccharides in the cell lysate during the purification. In some embodiments, the positively charged polysaccharide, the neutral polysaccharide, the negatively charged polysaccharide, or the combination thereof are not substantially precipitated during the purification. In some embodiments, the positively charged polysaccharide, the neutral polysaccharide, the negatively charged polysaccharide, or the combination thereof are not isolated from each other.

In some embodiments, greater than 90% (v/v) of negatively charged polysaccharides are in the first supernatant and less than 10% (v/v) of negatively charged polysaccharides are in the first precipitate. In some embodiments, greater than 98% (v/v) of negatively charged polysaccharides are on the first supernatant and less than 2% (v/v) of negatively charged polysaccharides are in the first precipitate.

In some embodiments, the percent yield of polysaccharides is greater than 30% relative to the polysaccharides in the cell lysate. In some embodiments, the percent yield of polysaccharides is greater than 40% relative to the polysaccharides in the cell lysate. In some embodiments, the percent yield of polysaccharides is greater than 50% relative to the polysaccharides in the cell lysate. In some embodiments, the percent yield of polysaccharides is greater than 60% relative to the polysaccharides in the cell lysate. In some embodiments, the percent yield of polysaccharides is greater than 70% relative to the polysaccharides in the cell lysate. In some embodiments, the percent yield of polysaccharides is 35% to 80% relative to the polysaccharides in the cell lysate.

In some embodiments, the cell lysate is derived from a bacterial cell or a fungal cell. In some embodiments, the cell is a *Staphylococcus* cell, *Streptococcus* cell, Salmonella cell, Neisseria cell, *Mycobacterium* cell, or *Aureobasidium* cell.

In some embodiments, the cell is a *Streptococcus* cell. In some embodiments, the *Streptococcus* cell is serotype 1, 2, 3, 4, 5, 6A, 6B, 7F, 8, 9N, 9V, 10A, 11A, 12F, 14, 15A, 15B, 17F, 18C, 19A, 19F, 20A, 22F, 23F, or 33F. In some embodiments, the *Streptococcus* cell is serotype 3 or 4.

In some embodiments, the disclosure provides a method of purifying polysaccharides from a cell lysate, the method comprising: (a) partially purifying the cell lysate comprising an impurity and a polysaccharide to obtain a clarified crude lysate; (b) mixing the clarified crude lysate with a neutralization solution comprising about 400 mM sodium chloride (NaCl) to form a neutralized lysate; (c) mixing the neutralized lysate with about 1.0% v/v cetyltrimethylammonium bromide (CTAB) to form a first supernatant and a first precipitate; (d) separating the first precipitate from the first supernatant; (e) mixing the first supernatant with potassium iodide (KI) to a second precipitate and a second supernatant; and (f) separating the second precipitate from the second supernatant, wherein the polysaccharide is substantially located in the second supernatant.

In some embodiments, the disclosure provides a method of making a polysaccharide vaccine, the method comprising purifying a polysaccharide according to a method provided herein, to obtain the polysaccharide vaccine. In some embodiments, the polysaccharide comprises chitosan, glucan, mannose, inulin, galactose, galacturonic acid, 2-acetamido-4-amino-2,4,6-trideoxygalactose (AATGalp), glucuronic acid, glucose, rhamnose, N-acetylmannosamine (ManNAc), N-acetyl-L-fucosamine (FucNAc), beta-galactofuranose (beta-Galf), or combination thereof. In some embodiments, the polysaccharide is further conjugated with a protein or polypeptide.

In some embodiments, the disclosure provides a vaccine comprising a polysaccharide purified by a method provided herein. In some embodiments, the polysaccharide comprises chitosan, glucan, mannose, inulin, galactose, galacturonic acid, 2-acetamido-4-amino-2,4,6-trideoxygalactose (AATGalp), glucuronic acid, glucose, rhamnose, N-acetylmannosamine (ManNAc), N-acetyl-L-fucosamine (FucNAc), beta-galactofuranose (beta-Galf), or combination thereof.

In some embodiments, the disclosure provides a delivery system comprising a polysaccharide purified by a method provided herein. In some embodiments, the polysaccharide comprises pullulan, hyaluronic acid, alginate, chitosan, dextran, cellulose, or combination thereof.

In some embodiments, the disclosure provides a pharmaceutical composition comprising a polysaccharide purified by a method provided herein. In some embodiments, the polysaccharide comprises chitosan.

In some embodiments, the disclosure provides a polysaccharide purified by a method provided herein.

DETAILED DESCRIPTION OF THE INVENTION

The present disclosure relates to methods of purifying polysaccharides from a cell.

As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability, depending on the situation.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps. It is contemplated that any embodiment discussed in this specification can be implemented with respect to any method, system, compound, e.g., polysaccharide, and/or composition of the present disclosure. Furthermore, compositions, systems, and/or compounds, e.g., polysaccharides, of the present disclosure can be used to achieve methods of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

As used herein, a "polysaccharide" is a polymeric carbohydrate compound comprising long chains of monosaccharide units bound together by glycosidic linkages. Polysaccharides can range in structure from linear to highly branched. Polysaccharides can include, e.g., "storage" polysaccharides such as starch, glycogen and the like, and "structural" polysaccharides such as cellulose, chitin, arabinoxylans, pectin, and the like. Polysaccharides can be charged or neutral. A "charged" polysaccharide carries a charged group in the molecule, which includes both negatively charged (acidic) and positively charged polysaccharides. Negatively charged polysaccharides can contain, e.g., carboxyl groups and/or sulfuric ester groups. Positively charged polysaccharides can contain, e.g., a protonated free amino group. Polysaccharides are further described in, e.g., Guo et al., DOI: 10.5772/intechopen.71570.

Polysaccharide of the present disclosure may be produced by a cell. For example, certain bacteria, typically pathogenic bacteria, produce a thick, mucous-like, layer of polysaccharide. This polysaccharide layer, sometimes referred to as a "capsule" or "surface capsule," can be a protective mechanism that cloaks antigenic proteins on the bacterial surface that would otherwise provoke an immune response and thereby leading to destruction of the bacteria. In general, bacterial capsular polysaccharides are water-soluble, sometimes acidic, and have molecular weights of about 100 to about 2000 kDa. The bacterial capsular polysaccharides are typically linear and can include regularly repeating subunits of one to six monosaccharides. Bacterial capsular polysaccharides have wide structural diversity. In some embodiments, polysaccharides, e.g., bacterial capsular polysaccharides, are used in the production of a vaccine, e.g., for protection against the bacteria, and/or as an adjuvant. In some embodiments, a polysaccharide is present inside and/or on the surface of a cell described herein, e.g., a bacterial cell. In some embodiments, a polysaccharide is present in a cell lysate described herein.

As used herein, "precipitation" refers to a process in which a solid is formed in a solution, e.g., a liquid solution. The solid formed is referred to as the "precipitate," while the liquid is the "supernatant." In some embodiments, precipitation can be induced by adding an agent referred to herein as the "precipitant." In some embodiments, precipitation is used to separate one component of a solution from another component. For example, precipitation can be used to separate the polysaccharides from undesired impurities in a cell lysate as described herein, thereby "purifying" the polysaccharide from the cell lysate. One of skill in the art will understand that the term "purifying" refers to the removal of some or all of an impurity and does not necessarily refer to compositions lacking impurities.

As used herein, a "polynucleotide" means a polymeric compound including covalently linked nucleotides. Polynucleotides include, e.g., DNA, RNA, or combination thereof. In some embodiments, polynucleotides are present inside and/or on the surface of a cell described herein, e.g., a bacterial cell. In some embodiments, polynucleotides are present in a cell lysate described herein. In some embodiments, polynucleotides are considered an impurity of the cell lysate described herein.

As used herein, a "protein" or "polypeptide" means a polymeric form of amino acids of any length. Proteins include, e.g., structural proteins, enzymes, membrane or membrane-associated proteins, transporters, receptors, and the like. In some embodiments, proteins of the present disclosure are present inside and/or on the surface of a cell described herein, e.g., a bacterial cell. In some embodiments, proteins are present in a cell lysate described herein. In some embodiments, proteins are considered an impurity of the cell lysate described herein. In some embodiments, proteins or polypeptides are used as a vaccine antigen as described herein.

In some embodiments, the present disclosure provides an efficient and simplified method to separate polysaccharides from undesired impurities such as polynucleotides and polypeptides. For example, the present method can purify any type of polysaccharide, independent of the charge of the polysaccharide (e.g., positively charged, negatively charged, and neutral). The present method also reduces the number of steps in the polysaccharide purification process. In some embodiments, the method does not comprise precipitating, then resolubilizing the polysaccharide, as described, e.g., in U.S. Pat. No. 5,714,354. Precipitating and resolubilizing the polysaccharide can lead to reproducibility issues, since it may be difficult to ensure complete precipitation and resolubilization of the polysaccharide. Thus, the present methods reduce complexity of currently used purification methods and improves efficiency. For example, for manufacturers of pharmaceuticals such as vaccines, delivery systems, and/or pharmaceutical compositions, the ability to use a single, streamlined process for purification of any type of polysaccharide can greatly reduce the number of equipment and maintenance thereof, use equipment more efficiently, increase production times, lower processing and labor costs, simplify personnel training, reduce the amount of different inspections and certification, improve manufacturability and scaling, etc.

In some embodiments, the same method is used to purify different types of polysaccharides. For example, the different polysaccharides may differ in charge, size, type of monosaccharide units, source (e.g., organism, serotype), etc. In some embodiments, using the same method to purify different polysaccharides increases efficiency, e.g., by reducing steps in the purification process specific to a certain type of polysaccharide. In some embodiments, using the same method to purify different polysaccharides increases consistency, e.g., by using the same neutralization and precipitation solutions and the same steps regardless of the type of polysaccharide. In some embodiments, using the same method to purify different polysaccharides simplifies the process characterization study, which is typically required in the commercialization of a new drug. For example, for drug product commercialization, manufacturers must validate the drug's manufacturing process, which ensures that the manufacturing process delivers consistent product quality and that the patient is not at risk. Thus, in embodiments wherein the same method is used to purify different polysaccharides, the method would only need to be validated once, even when the polysaccharides may be used in different drug products, thereby greatly reducing costs to the manufacturer and ultimately to the customer, e.g., patient.

In some embodiments, the disclosure provides a method of purifying polysaccharides from a cell lysate, the method comprising (a) partially purifying the cell lysate comprising a polysaccharide and an impurity to obtain a clarified crude lysate; (b) mixing the clarified crude lysate with a neutralization solution comprising about 100 mM to about 2 M salt to form a neutralized lysate; (c) mixing the neutralized lysate with a precipitation solution comprising about 0.1% v/v to about 6% v/v cetyltrimethylammonium bromide (CTAB) to form a first supernatant and a first precipitate; and (d) separating the first precipitate from the first supernatant, wherein the polysaccharide is substantially located in the first supernatant.

In some embodiments, the cell lysate is obtained from lysing a cell. In some embodiments, the cell is lysed using mechanical disruption, liquid homogenization, sonication, freeze-thaw, manual grinding, osmotic lysis, chemical lysis (including, e.g., use of antibiotics, chelating agents, chaotropic agents, and/or solvents), or combination thereof. Methods of lysing cells are known in the art and described, e.g., in Walker, J. M. *The Protein Protocols Handbook, 3ʳᵈ Ed.* New York (NY): Springer-Verlag New York, LLC. In some embodiments, the cell lysate comprises a mixture of the intracellular and surface components of the cell. In some embodiments, the cell lysate comprises an impurity and a polysaccharide.

In some embodiments, the cell lysate is obtained from lysing a bacterial cell. In some embodiments, the bacterial cell is an encapsulated bacterial cell. An encapsulated bacterial cell has a surface capsule comprising a polysaccharide. In some embodiments, the polysaccharide of the bacterial cell surface generates an immune response from a host cell of the bacteria. In some embodiments, the polysaccharide is used to generate a vaccine against the bacteria. In some embodiments, the polysaccharide is used as an adjuvant in a vaccine.

Exemplary bacteria that have a surface capsule comprising a polysaccharide include, but are not limited to, *Staphylococcus aureus, Streptococcus pneumoniae, Streptococcus agalactiae* and other group A streptococci (GAS), *Streptococcus pyogenes* and other group B streptococci (GB S), *Salmonella enterica, Salmonella typhi, Salmonella paratyphi, Mycobacterium tuberculosis, Neisseria meningitidis, Haemophilus influenzae, Klebsiella pneumonia,* and *Escherichia coli.* In some embodiments, the bacterial cell is a *Staphylococcus* cell, a *Streptococcus* cell, a *Salmonella* cell, a *Neisseria* cell, or a *Mycobacterium* cell. In some embodiments, the bacterial cell is a *Streptococcus* cell. In some embodiments, the bacterial cell is a *Streptococcus pneumoniae* cell, a *Streptococcus agalactiae* cell, or a *Streptococcus pyogenes* cell. In some embodiments, the bacterial cell is a *Staphylococcus* cell. In some embodiments, the bacterial cell is a *Staphylococcus aureus* cell. In some embodiments, the bacterial cell is a *Salmonella* cell. In some embodiments, the bacterial cell is a *Salmonella enterica* cell. In some embodiments, the bacterial cell is a *Salmonella* cell. In some embodiments, the bacterial cell is a *Salmonella enterica* cell, e.g., a *Salmonella typhi* cell or a *Salmonella paratyphi* cell. In some embodiments, the bacterial cell is a *Neisseria* cell. In some embodiments, the bacterial cell is a *Neisseria meningitidis* cell. In some embodiments, the bacterial cell is a *Mycobacterium* cell. In some embodiments, the bacterial cell is a *Mycobacterium tuberculosis* cell. Bacteria include numerous serotypes corresponding to different antigens on their cell surface. In some embodiments, different serotypes of a bacterial organism have varying degrees of virulence. In some embodiments, the bacterial cell is a virulent bacterial cell. In some embodiments, the bacterial cell is a *Staphylococcus aureus* cell of serotype 1, 2, 5, 8, 336, or NT. In some embodiments, the bacterial cell is a *Salmonella* cell of serotype Typhi, Typhimurium, Choleraesuis, Schwarzengrund, Derby, Haifa, Stanley, Newport, Virchow, Paratyphi, Singapore, Agona, Panama, Blockley, Anatum, Infantis, Enteritidis, Heidelberg, Muenchen, Javiana, Montevideo, Thompson, or Oranienburg. In some embodiments, the bacterial cell is a *Neisseria meningitidis* cell of serotype A, B, C, W, or Y. In some embodiments, the bacterial cell is a *Mycobacterium tuberculosis* cell of serotype 4, 8, 9, or NT. In some embodiments, the bacterial cell is a *Streptococcus* cell of serotype 1, 2, 3, 4, 5, 6A, 6B, 7F, 8, 9A, 9L, 9N, 9V, 10A, 11A, 11B, 11C, 11D, 11F, 12F, 14, 15A, 15B, 15C, 15F, 17F, 18A, 18B, 18C, 18F, 19A, 19B, 19C, 19F, 20A, 22F, 23A, 23B, 23F, or 33F. In some embodiments, the *Streptococcus* cell is serotype 3 or serotype 4. In some embodiments, the *Streptococcus* cell is serotype 3. In some embodiments, the *Streptococcus* cell is serotype 4.

In some embodiments, the cell lysate is obtained from lysing a fungal cell. In some embodiments, the fungal cell has a cell wall comprising a polysaccharide. In some embodiments, the polysaccharide of the fungal cell wall generates an immune response from a host cell of the fungus. In some embodiments, the polysaccharide of the fungal cell wall is used to generate a vaccine against the fungus. In some embodiments, the polysaccharide of the fungal cell wall is used as an adjuvant in a vaccine. Exemplary fungi that have a cell wall comprising a polysaccharide include, but are not limited to, *Aspergillus fumigatus, Candida albicans, Cryptococcus neoformans, Histoplasma capsulatum,* and *Aureobasidium pullulans.* In some embodiments, the fungal cell is an *Aureobasidium* cell. In some embodiments, the fungal cell is an *Aureobasidium pullulans* cell. In some embodiments, the fungal cell is *Aureobasidium pullulans* var. pullulans. In some embodiments, the fungal cell is *Aureobasidium pullulans* cell var. *melanogenicum.* In some embodiments, the fungal cell is *Aureobasidium pullulans* strain MC 571, strain MC 573, strain MC 574, strain MC 576, strain MC 711, strain MC 737, strain MC 745, strain MC 767, strain CBS 701.76, or strain CBS 105.22. In some embodiments, the fungal cell is an Aspergillus fumigatus cell. In some embodiments, the fungal cell is a *Candida albicans* cell. In some embodiments, the fungal cell is a *Candida albicans* cell of serotype A or B. In some embodiments, the fungal cell is a *Cryptococcus neoformans* cell. In some embodiments, the fungal cell is a *Cryptococcus neoformans* cell of serotype A, D, or AD hybrid. In some embodiments, the fungal cell is a *Histoplasma capsulatum* cell. In some embodiments, the fungal cell is a *Histoplasma capsulatum* cell of serotype 1, 2, 3, 4, or 5.

In some embodiments, the polysaccharide in the cell lysate is from the surface of the cell. In some embodiments, the polysaccharide is a neutral polysaccharide. In some embodiments, the polysaccharide is a positively charged polysaccharide. In some embodiments, the polysaccharide is a negatively charged polysaccharide. In some embodiments, the cell lysate comprises a positively charged polysaccharide, a neutral polysaccharide, a negatively charged polysaccharide, or combination thereof. Charged polysaccharides (positively charged or negatively charged), and neutral polysaccharides are described herein.

In some embodiments, the polysaccharide is a bacterial surface polysaccharide. In some embodiments, the polysaccharide is a fungal cell wall polysaccharide. In some embodiments, the polysaccharide comprises hyaluronic acid, glucuronic acid, N-acetylglucosamine, sialic acid, galactose, glucose, N-acetylmannosamine, N-acetylfucosamine, polyribosyl ribitol phosphate (PRP), galactan, rhamnose, hexauonic acid, mannooctulonic acid, phosphate, cellulose, pullulan, β-glucan, lectin, dectin-1, dectin-2, galectin-3, mannan, chitin, galactomannan, a-glucan, galactosaminegalactan, galactoxylomannan, glucuronoxylomannan, chitosan, glucan, mannose, inulin, galactose, galacturonic acid, 2-acetamido-4-amino-2,4,6-trideoxygalactose (AATGalp), glucuronic acid, glucose, rhamnose, N-acetylmannosamine (ManNAc), N-acetyl-L-fucosamine (FucNAc), beta-galactofuranose (beta-Galf), or any combination thereof. In some embodiments, the polysaccharide comprises chitosan, glucan, mannose, inulin, galactose, galacturonic acid, 2-acetamido-4-amino-2,4,6-trideoxygalactose (AATGalp), glucuronic acid, glucose, rhamnose, N-acetylmannosamine (ManNAc), N-acetyl-L-fucosamine (FucNAc), beta-galactofuranose (beta-Galf), or any combination thereof. Further polysaccharides are provided in, e.g., Morris et al., Encyclopedia of Microbiology $3^{rd}$ Edition, ed. M. Schaechter, 482-494 (2009); and Snarr et al., J Fungi 3(3):47 (2017).

In some embodiments, the cell lysate comprises a polysaccharide described herein and an impurity. In some embodiments, the impurity comprises an intracellular component. In some embodiments, the impurity comprises a polynucleotide, a polypeptide, a lipid, a macromolecule, a small molecule, a signaling molecule, a metabolite, a membrane component, or combination thereof. In some embodiments, the impurity comprises a polynucleotide. In some embodiments, the impurity comprises DNA, RNA, or combination thereof. In some embodiments, the impurity comprises any non-polysaccharide component of the cell.

In some embodiments, one or more impurities have similar physical and/or chemical properties as the polysaccharide, e.g., similar molecular weight, structural features (e.g., shape, polymerization state and the like), charge, density, and/or solubility in water. In some embodiments, one or more impurities have the same charge as the polysaccharide. In some embodiments, one or more impurities are positively charged. In some embodiments, one or more impurities are negatively charged. In some embodiments, one or more impurities are neutral, i.e., has no charge. In some embodiments, the cell lysate comprises one or more positively charged impurities, a positively charged polysaccharide, a neutral polysaccharide, and a negatively charged polysaccharide. In some embodiments, the cell lysate comprises one or more negatively charged impurities, a positively charged polysaccharide, a neutral polysaccharide, and a negatively charged polysaccharide. In some embodiments, the cell lysate comprises one or more neutral impurities, a positively charged polysaccharide, a neutral polysaccharide, and a negatively charged polysaccharide. In some embodiments, the cell lysate comprises one or more polynucleotide impurities, a positively charged polysaccharide, a neutral polysaccharide, and a negatively charged polysaccharide. In some embodiments, the one or more polynucleotide impurities include negatively charged polynucleotide impurity. In some embodiments, the negatively charged polynucleotide impurity is DNA.

In some embodiments, one or more impurities are not separable from the polysaccharide by chromatography, filtration, or centrifugation of the cell lysate, e.g., due to their similarities in physical and/or chemical properties. In some embodiments, one or more impurities can be precipitated by a precipitant, while the polysaccharide does not form a precipitate in the presence of the precipitant, thereby separating the one or more impurities from the polysaccharide. In alternative embodiments, one or more impurities remain in solution in the presence of a precipitant while the polysaccharide forms a precipitate, thereby separating the one or more impurities from the polysaccharide. In some embodiments, one or more impurities include a polynucleotide impurity. In some embodiments, the polynucleotide impurity is DNA.

In some embodiments, the cell lysate comprising a polysaccharide and an impurity is partially purified to obtain a clarified crude lysate. In some embodiments, partially purifying the cell lysate comprises pH adjustment, precipitation, centrifugation, filtration, or combination thereof. In some embodiments, the precipitation comprises adjusting the pH such that one or more impurities form a precipitate. In some embodiments, the centrifugation separates the soluble fraction from the insoluble fraction (e.g., the precipitate) of the cell lysate, i.e., the centrifugation clarifies the cell lysate. In some embodiments, the filtration comprises depth filtration, tangential flow filtration (TFF), sterile filtration, or combination thereof. In some embodiments, the filtration comprises depth filtration. The skilled artisan can select the appropriate purification steps and parameters thereof to obtain a clarified crude lysate comprising a polysaccharide. In some embodiments, the clarified crude lysate comprises an impurity not removed by the partial purification steps described herein. In some embodiments, the clarified crude lysate comprises a polysaccharide and an impurity.

In some embodiments, the clarified crude lysate is mixed with a neutralization solution comprising a salt to form a neutralized lysate. In some embodiments, the neutralized lysate comprises a polysaccharide and an impurity. In some embodiments, the salt provides a chemical environment in which a charged compound, e.g., a charged polysaccharide, can behave like a neutral polysaccharide. Thus, in some embodiments, the salt neutralizes the charged compound, e.g., charged polysaccharide. In some embodiments, the neutralization comprises about 100 mM to about 2 M, about 150 mM to about 1.5 M, about 200 mM to about 1 M, about 200 mM to about 800 mM, about 250 mM to about 750 mM, about 250 mM to about 700 mM, about 300 mM to about 600 mM, about 300 mM to about 500 mM, about 400 mM to about 500 mM, or about 400 mM to about 450 mM salt. In some embodiments, the neutralization solution comprises about 100 mM, about 150 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, about 550 mM, about 600 mM, about 650 mM, about 700 mM, about 750 mM, about 800 mM, about 850 mM, about 900 mM, about 950 mM, about 1 M, about 1.1 M, about 1.2 M, about 1.3 M, about 1.4 M, about 1.5 M, about 1.6 M, about 1.7 M, about 1.8 M, about 1.9 M, or about 2 M salt.

In some embodiments, the concentration of salt in the neutralization solution is selected based on one or more of the number and type of cells, the volume of the clarified crude lysate, the amount of polysaccharide (predicted, estimated, or measured), the amount of impurity (predicted, estimated, or measured), and additional components that may be present in the clarified crude lysate. In some embodiments, the concentration of salt in the neutralization solution is sufficient to neutralize a charged compound, e.g., a charged polysaccharide, in the clarified crude lysate. In some embodiments, the salt does not substantially precipitate the polysaccharide in the neutralized lysate.

In some embodiments, the salt is a chaotropic salt. In some embodiments, the salt is a sodium salt. In some embodiments, the salt is a potassium salt. In some embodiments, the salt is an ammonium salt. In some embodiments, the salt is a halide salt. In some embodiments, the salt is a chloride salt. In some embodiments, the salt is a phosphate salt. In some embodiments, the salt is NaCl, KCl, $CH_4Cl$, $NaPO_3$, $NH_4Cl$, $MgCl_2$, $CaCl_2$, $Na_2PO_4$, or combination thereof. In some embodiments, the neutralization solution comprises NaCl.

In some embodiments, the neutralization solution comprises about 100 mM to about 2 M, about 150 mM to about 1.5 M, about 200 mM to about 1 M, about 200 mM to about 800 mM, about 250 mM to about 750 mM, about 250 mM to about 700 mM, about 300 mM to about 600 mM, about 300 mM to about 500 mM, about 400 mM to about 500 mM, or about 400 mM to about 450 mM NaCl. In some embodiments, the neutralization solution comprises about 100 mM, about 150 mM, about 200 mM, about 225 mM, about 250 mM, about 275 mM, about 300 mM, about 325 mM, about 350 mM, about 375 mM, about 400 mM, about 425 mM, about 440 mM, about 450 mM, about 475 mM, about 500 mM, about 550 mM, about 600 mM, about 650 mM, about 700 mM, about 750 mM, about 800 mM, about 850 mM, about 900 mM, about 950 mM, about 1 M, about 1.1 M, about 1.2 M, about 1.3 M, about 1.4 M, about 1.5 M, about 1.6 M, about 1.7 M, about 1.8 M, about 1.9 M, or about 2 M NaCl. In some embodiments, the neutralization solution comprises about 440 mM NaCl. In some embodiments, the amount of NaCl in the neutralization solution is sufficient to neutralize a charged compound, e.g., a charged polysaccharide, in the clarified crude lysate. In some embodiments, the NaCl in the neutralization solution does not substantially precipitate the polysaccharide in the neutralized lysate.

In some embodiments, the mixing of the clarified crude lysate with the neutralization solution to form a neutralized lysate is performed simultaneously with a filtration step. In some embodiments, the mixing of the clarified crude lysate with the neutralization solution to form a neutralized lysate is performed prior to a filtration step. In some embodiments, the filtration comprises tangential flow filtration (TFF). In some embodiments, the TFF buffer comprises the neutralization solution, thereby performing the mixing and the filtration steps simultaneously. In some embodiments, the filtration step is performed prior to the mixing of the neutralized lysate with the precipitation solution.

In some embodiments, the neutralized lysate is mixed with a precipitation solution comprising a precipitant. In some embodiments, the precipitation solution comprises cetyltrimethylammonium bromide (CTAB). In some embodiments, the precipitant is CTAB. In some embodiments, the polysaccharide does not substantially form a precipitate in the precipitation solution. In some embodiments, one or more impurities are substantially in a first precipitate in the precipitation solution. In some embodiments, a polynucleotide impurity forms a first precipitate when the precipitation solution is mixed with the neutralized lysate, and the polysaccharide of the neutralized lysate remains soluble when the precipitation solution is mixed with the cell lysate. Thus, in some embodiments, one or more impurities are in the first precipitate. In some embodiments, the polysaccharide is substantially located in the first supernatant. In some embodiments, the positively charged polysaccharide, neutral polysaccharide, negatively charged polysaccharide, or combination thereof are in the first supernatant. In some embodiments, one or more impurities include a negatively charged polynucleotide impurity. In some embodiments, the negatively charged polynucleotide impurity is DNA.

One of skill in the art will appreciate that during precipitation of impurities, 100% of a given impurity is usually not precipitated. Thus, the term "substantially" when referring to precipitating impurities refers to the amount of a given impurity the skilled artisan would expect to precipitate, e.g., greater than about 60%, greater than about 70%, greater than about 80%, greater than about 90%, or greater than about 95% of the given impurity.

It was discovered that upon addition of CTAB to a neutralized lysate as described herein, polynucleotides (e.g., DNA) can be selectively precipitated, while polysaccharides (e.g., positively charged, negatively charged, neutral polysaccharides, or combination thereof) remained in solution. Without being bound by theory, it is believed that the CTAB causes the negatively charged DNA to precipitate, while allowing polysaccharides of any charge (including negatively charged polysaccharides) to substantially remain in solution because charged polysaccharides (e.g., negatively charged polysaccharides) behave like neutral polysaccharides in the neutralized lysate, as described herein. By "substantially in solution," it is meant that greater than about 50%, greater than about 55%, greater than about 60%, greater than about 65%, greater than about 70%, greater than about 75%, greater than about 80%, greater than about 85%, greater than about 90%, greater than about 91%, greater than about 92%, greater than about 93%, greater than about 94%, greater than about 95%, greater than about 96%, greater than about 97%, greater than about 98%, greater than about 99%, or about 100% of the polysaccharides in the lysed cell are in the first and/or second supernatant. Thus, the present disclosure provides improved efficiency and simplicity for separating polysaccharides from impurities.

In some embodiments, the precipitation solution comprises greater than 0.1% v/v/CTAB, or 0.1% v/v to 20% v/v CTAB. In some embodiments, the precipitation solution comprises about 0.1% v/v to about 10% v/v CTAB, about 0.1% v/v to about 6% v/v CTAB, or about 0.2% v/v to about 5% v/v CTAB, or about 0.5% v/v to about 4% v/v CTAB, or about 1% v/v to about 3% v/v CTAB, or about 1.5% v/v to about 2.5% v/v CTAB, or about 1% v/v to about 2% v/v CTAB. In some embodiments, the precipitation solution comprises about 0.1% v/v, about 0.2% v/v, about 0.3% v/v, about 0.4% v/v, about 0.5% v/v, about 0.6% v/v, about 0.7% v/v, about 0.8% v/v, about 0.9% v/v, about 1% v/v, about 1.1% v/v, about 1.2% v/v, about 1.3% v/v, about 1.4% v/v, about 1.5% v/v, about 1.6% v/v, about 1.7% v/v, about 1.8% v/v, about 1.9% v/v, about 2% v/v, about 2.1% v/v, about 2.2% v/v, about 2.3% v/v, about 2.4% v/v, about 2.5% v/v, about 2.6% v/v, about 2.7% v/v, about 2.8% v/v, about 2.9% v/v, about 3.0% v/v, about 3.1% v/v, about 3.2% v/v, about 3.3% v/v, about 3.4% v/v, about 3.5% v/v, about 3.6% v/v, about 3.7% v/v, about 3.8% v/v, about 3.9% v/v, or about 4% v/v CTAB.

In some embodiments, the concentration of CTAB in the precipitation solution is selected based on one or more of: the number and type of cells, the volume of the neutralized lysate, the amount of polysaccharide (predicted, estimated, or measured), the amount of impurity (predicted, estimated, or measured), and additional components that may be present in the neutralized lysate. In some embodiments, the amount of CTAB in the precipitation solution is sufficient to precipitate the impurity. In some embodiments, the amount of CTAB in the precipitation solution is sufficient to precipitate DNA. In some embodiments, the CTAB in the precipitation solution does not substantially precipitate the polysaccharide. In some embodiments, the polysaccharide is substantially in the first supernatant. In some embodiments, the positively charged polysaccharide, the neutral polysaccharide, the negatively charged polysaccharide, or combination thereof are substantially located in the first supernatant. In some embodiments, the impurity, e.g., DNA, is substantially in the first precipitate.

In some embodiments, the mixing of the neutralized lysate with the precipitation solution is performed by shaking, stirring, pumping, or combination thereof. In some embodiments, mixing of the neutralized lysate with the precipitation solution promotes formation of the precipitate. In some embodiments, mixing of the neutralized lysate with the precipitation solution improves separation of the first precipitate from the first supernatant.

In some embodiments, the positively charged polysaccharide, negatively charged polysaccharide, neutral polysaccharide, or combination thereof can be removed from a polynucleotide impurity, e.g., DNA, by precipitation of the polynucleotide impurity without a chromatography step. Therefore, in some embodiments, the method does not comprise a chromatography step prior to the separating of the first precipitate from the first supernatant. Non-limiting examples of chromatography include anion exchange chromatography, cation exchange chromatography, hydrophobic interaction chromatography, affinity chromatography, and size exclusion chromatography.

In some embodiments, the first precipitate is separated from the first supernatant after mixing of the neutralized lysate with the precipitation solution. In some embodiments, the separating is performed by centrifugation, filtration, decanting, or combination thereof. In some embodiments, the separating is performed by centrifugation or filtration. One of ordinary skill in the art is capable of choosing the parameters of the centrifugation, e.g., speed and duration; or the filtration technique, e.g., vacuum filtration, gravity filtration, or combination thereof; or the decanting apparatus, e.g., container type and decant angle; to adequately separate the first precipitate and first supernatant.

In some embodiments, the CTAB and the polysaccharide are in the first supernatant after the mixing and separating. In downstream processing of the polysaccharides provided herein, presence of CTAB may not be desirable. Thus, in some embodiments, the method further comprises removing the CTAB from the first supernatant after separating of the first precipitate and first supernatant. In some embodiments, the first supernatant is subjected to ultrafiltration, diafiltration, or combination thereof to produce a retentate and a permeate, wherein the polysaccharide is in the retentate, and the CTAB is in the permeate. In general, ultrafiltration and/or diafiltration (UF/DF) produces a "permeate," which contains materials capable of passing through the UF/DF membrane, and a "retentate," which contains materials that do not pass the UF/DF membrane. In some embodiments, the UF/DF membrane pore size is selected such that the CTAB passes through the membrane and the polysaccharide does not pass through the membrane. In such embodiments, the method provides the benefit of removing CTAB from the first supernatant without a second precipitation step, thereby simplifying the polysaccharide purification process. In some embodiments, the positively charged polysaccharide, the neutral polysaccharide, the negatively charged polysaccharide, or combination thereof are substantially located in the retentate.

While one or more undesired impurities are generally removed from the cell lysate by precipitation with the precipitation solution, additional soluble impurities may remain in the first supernatant and/or the retentate comprising the polysaccharide. These additional impurities can include, for example, proteins, peptides, and proteinaceous compounds, and small molecules such as, e.g., signaling molecules or metabolites. In some embodiments, the method further comprises removing one or more impurities from the retentate. In some embodiments, the method further comprises subjecting the retentate to filtration to remove one or more impurities. In some embodiments, the one or more impurities comprise a protein. In some embodiments, the filtration separates the one or more impurities from the polysaccharide by their differential adsorption to the filter or filtration resin. In some embodiments, the filtration separates the one or more impurities from the polysaccharide by molecular weight. In some embodiments, the filtration comprises carbon filtration. Non-limiting examples of carbon filters include CUNO NORIT®, ZETA PLUS™, VAPLOCK™, and the like.

In some embodiments, the method further comprises subjecting the retentate to chromatography. In some embodiments, the retentate is subjected to chromatography following the filtration, e.g., carbon filtration. In some embodiments, the chromatography removes one or more impurities from the second supernatant. In some embodiments, the impurity comprises a protein. In some embodiments, the chromatography is anion exchange, cation exchange, hydrophobic interaction, affinity, size exclusion chromatography, or combination thereof. In some embodiments, the chromatography comprises ceramic hydroxyapatite type (CHT) chromatography, hydrophobic interaction chromatography (HIC), or combination thereof. In some embodiments, the chromatography is CHT chromatography, e.g., using the CHT resin from BIORAD LABORATORIES. CHT resin typically includes a combination of ion exchange (e.g., cation exchange) and affinity (e.g., calcium affinity) resins.

In some embodiments, the method further comprises subjecting the retentate to at least two chromatography steps. Thus, in some embodiments, the chromatography comprises CHT chromatography and HIC. In some embodiments, the method comprises subjecting the retentate to CHT chromatography, followed by hydrophobic interaction chromatography (HIC). It was unexpectedly discovered that the two sequential chromatography steps advantageously improved removal of undesired impurities in the solution containing the desired polysaccharide. Examples of ligands for HIC resins include, but are not limited to, phenyl, octyl, and butyl groups. Suitable HIC resins include, e.g., SARTOBIND Membranes from SARTORIUS, G-SEP Agarose Fast Flow resins from G-BIOSCIENCES, and CAPTO and SEPHAROSE resins from GE. In some embodiments, the HIC is performed using a phenyl membrane resin.

In some embodiments, the carbon filtration is performed using the same device as the chromatography. For example, the retentate can be passed through a carbon filtration column followed by a chromatography column without an intermediate step of collecting the carbon-filtered retentate, then performing the chromatography.

In some embodiments, the first supernatant comprising the CTAB and polysaccharide is mixed with a second precipitation solution. In some embodiments, the second precipitation solution comprises a different precipitant from the precipitation solution. In some embodiments, the first supernatant is mixed with potassium iodide (KI) to form a second precipitate and a second supernatant. In some embodiments, KI forms a precipitate with CTAB, but not the polysaccharide. In some embodiments, the polysaccharide is substantially in the second supernatant, and the CTAB is substantially in the second precipitate. In some embodiments, the positively charged polysaccharide, the neutral polysaccharide, the negatively charged polysaccharide, or combination thereof are substantially located in the second supernatant. In some embodiments, the second precipitation solution comprises about 0.1% v/v to about 6% v/v KI, or about 0.2% v/v to about 5% v/v KI, or about 0.5% v/v to about 4% v/v KI, or about 1% v/v to about 3% v/v KI, or about 1.5% v/v to about 2.5% v/v KI, or about 1% v/v to about 2% v/v KI, or about 0.5% v/v to about 1% v/v KI. In some embodiments, the amount of KI is selected based on the amount of CTAB in the first supernatant. The appropriate concentration of KI to adequately form a precipitate with substantially all of the CTAB, but substantially none of the polysaccharide, can be selected by the skilled artisan.

In some embodiments, the method does not comprise a chromatography step prior to the addition of KI to the first supernatant. In some embodiments, the method does not comprise an anion exchange chromatography, cation exchange chromatography, hydrophobic interaction chromatography, affinity chromatography, or size exclusion chromatography step prior to the addition of KI. In some embodiments, the method does not comprise an anion exchange chromatography step prior to the addition of KI. By not requiring a chromatography step prior to the addition of KI (i.e., the removal of CTAB by precipitation), the present method can further simplify the polysaccharide purification process.

In some embodiments, the method further comprises separating the second supernatant from the second precipitate. In some embodiments, separating the second supernatant from the second precipitate comprises centrifugation, filtration, decanting, or combination thereof. Methods of separating precipitates and supernatants are known in the field and provided herein. In some embodiments, the second supernatant is separated from the second precipitate by carbon filtration. Carbon filtration is further described herein. In some embodiments, the second supernatant is subjected to chromatography following the carbon filtration, in a similar manner as the retentate as described herein. In some embodiments, the chromatography is anion exchange, cation exchange, hydrophobic interaction, affinity, size exclusion chromatography, or combination thereof. In some embodiments, the chromatography comprises ceramic hydroxyapatite type (CHT) chromatography, hydrophobic interaction chromatography (HIC), or combination thereof. In some embodiments, the method comprises subjecting the second supernatant to CHT chromatography, followed by HIC. Examples of CHT chromatography resins and HIC ligands and resins are provided herein. In some embodiments, the HIC is performed using a phenyl membrane resin. In some embodiments, the carbon filtration is performed using the same device as the chromatography, as described herein.

In some embodiments, the polysaccharide is concentrated. In some embodiments, the concentration is performed after the chromatography, e.g., the CHT chromatography and HIC, of the retentate or the second supernatant as described herein. Concentration methods are known in the field and include, e.g., rotary evaporation, distillation, and ultrafiltration/diafiltration, e.g., tangential flow filtration. In some embodiments, the concentrating comprises ultrafiltration, diafiltration, or combination thereof. In some embodiments, the concentrating comprises tangential flow filtration, e.g., to form a concentrated polysaccharide. In some embodiments, the concentrated polysaccharide is substantially free of impurities.

The present methods advantageously allow effective separation of polysaccharides from undesired impurities, e.g., polynucleotides or proteins. In some embodiments, the polysaccharides remain substantially in solution throughout the method. As described herein, by "substantially in solution," it is meant that greater than about 50%, greater than about 55%, greater than about 60%, greater than about 65%, greater than about 70%, greater than about 75%, greater than about 80%, greater than about 85%, greater than about 90%, greater than about 91%, greater than about 92%, greater than about 93%, greater than about 94%, greater than about 95%, greater than about 96%, greater than about 97%, greater than about 98%, greater than about 99%, or about 100% of the polysaccharides in the cell lysate are in the first supernatant, the second supernatant, and/or the retentate.

In some embodiments, the present method does not comprise a precipitate containing greater than 10%, greater than 15%, greater than 20%, greater than 25%, greater than 35%, greater than about 40%, greater than about 45%, or greater than about 50% of the polysaccharides in the cell lysate during the purification. In some embodiments, the positively charged polysaccharide, the neutral polysaccharide, the negatively charged polysaccharide, or combination thereof are substantially not precipitated during the purification. By "substantially not precipitated," it is meant that less than 1%, less than 2%, less than 3%, less than 4%, less than 5%, less than 10%, less than 15%, less than 20%, less than 25%, less than 30%, less than 35%, or less than 40% of all polysaccharides in the cell lysate are located in the first precipitate, the second precipitate, and/or the permeate.

In some embodiments, the positively charged polysaccharide, the neutral polysaccharide, the negatively charged polysaccharide, or combination thereof are not substantially located in the first supernatant, the second supernatant, and/or the retentate. In some embodiments, the positively charged polysaccharide, the neutral polysaccharide, and the negatively charged polysaccharide are not isolated from each other during the method.

In some embodiments, polysaccharides located "substantially located in the first supernatant, the second supernatant, and/or the retentate" refers to greater than 60%, greater than 65%, greater than 70%, greater than 75%, greater than 80%, greater than 85%, greater than 90%, greater than 95%, greater than 96%, greater than 97%, greater than 98%, or greater than 99% of all polysaccharides in the cell lysate are located in the first supernatant, the second supernatant, and/or the retentate. Thus, in some embodiments, the phrase "substantially located in the first supernatant" means that greater than 60% (v/v) of negatively charged polysaccharides are in the first supernatant and less than 40% (v/v) of negatively charged polysaccharides are in the first precipitate. In some embodiments, greater than 65% (v/v) of negatively charged polysaccharides are in the first supernatant and less than 35% (v/v) of negatively charged polysaccharides are in the first precipitate. In some embodiments, greater than 70% (v/v) of negatively charged polysaccharides are in the first supernatant and less than 30% (v/v) of negatively charged polysaccharides are in the first precipitate. In some embodiments, greater than 75% (v/v) of negatively charged polysaccharides are in the first supernatant and less than 25% (v/v) of negatively charged polysaccharides are in the first precipitate. In some embodiments, greater than 80% (v/v) of negatively charged polysaccharides are in the first supernatant and less than 20% (v/v) of negatively charged polysaccharides are in the first precipitate. In some embodiments, greater than 85% (v/v) of negatively charged polysaccharides are in the first supernatant and less than 15% (v/v) of negatively charged polysaccharides are in the first precipitate.

In some embodiments, greater than 90% (v/v) of negatively charged polysaccharides are in the first supernatant and less than 10% (v/v) of negatively charged polysaccharides are in the first precipitate. In some embodiments, greater than 95% (v/v) of negatively charged polysaccharides are in the first supernatant and less than 5% (v/v) of negatively charged polysaccharides are in the first precipitate. In some embodiments, greater than 96% (v/v) of negatively charged polysaccharides are in the first supernatant and less than 4% (v/v) of negatively charged polysaccharides are in the first precipitate. In some embodiments, greater than 97% (v/v) of negatively charged polysaccharides are in the first supernatant and less than 3% (v/v) of negatively charged polysaccharides are in the first precipitate. In some embodiments, greater than 98% (v/v) of negatively charged polysaccharides are in the first supernatant and less than 2% (v/v) of negatively charged polysaccharides are in the first precipitate. In some embodiments, greater than 99% (v/v) of negatively charged polysaccharides are in the first supernatant and less than 1% (v/v) of negatively charged polysaccharides are in the first precipitate.

In some embodiments, greater than 60% (v/v) of positively charged polysaccharides are in the first supernatant and less than 40% (v/v) of positively charged polysaccharides are in the first precipitate. In some embodiments, greater than 65% (v/v) of positively charged polysaccharides are in the first supernatant and less than 35% (v/v) of positively charged polysaccharides are in the first precipitate. In some embodiments, greater than 70% (v/v) of positively charged polysaccharides are in the first supernatant and less than 30% (v/v) of positively charged polysaccharides are in the first precipitate. In some embodiments, greater than 75% (v/v) of positively charged polysaccharides are in the first supernatant and less than 25% (v/v) of positively charged polysaccharides are in the first precipitate. In some embodiments, greater than 80% (v/v) of positively charged polysaccharides are in the first supernatant and less than 20% (v/v) of positively charged polysaccharides are in the first precipitate. In some embodiments, greater than 85% (v/v) of positively charged polysaccharides are in the first supernatant and less than 15% (v/v) of positively charged polysaccharides are in the first precipitate.

In some embodiments, greater than 90% (v/v) of positively charged polysaccharides are in the first supernatant and less than 10% (v/v) of positively charged polysaccharides are in the first precipitate. In some embodiments, greater than 95% (v/v) of positively charged polysaccharides are in the first supernatant and less than 5% (v/v) of positively charged polysaccharides are in the first precipitate. In some embodiments, greater than 96% (v/v) of positively charged polysaccharides are in the first supernatant and less than 4% (v/v) of positively charged polysaccharides are in the first precipitate. In some embodiments, greater than 97% (v/v) of positively charged polysaccharides are in the first supernatant and less than 3% (v/v) of positively charged polysaccharides are in the first precipitate. In some embodiments, greater than 98% (v/v) of positively charged polysaccharides are in the first supernatant and less than 2% (v/v) of positively charged polysaccharides are in the first precipitate. In some embodiments, greater than 99% (v/v) of positively charged polysaccharides are in the first supernatant and less than 1% (v/v) of positively charged polysaccharides are in the first precipitate.

In some embodiments, greater than 60% (v/v) of neutral polysaccharides are in the first supernatant and less than 40% (v/v) of neutral polysaccharides are in the first precipitate. In some embodiments, greater than 65% (v/v) of neutral polysaccharides are in the first supernatant and less than 35% (v/v) of neutral polysaccharides are in the first precipitate. In some embodiments, greater than 70% (v/v) of neutral polysaccharides are in the first supernatant and less than 30% (v/v) of neutral polysaccharides are in the first precipitate. In some embodiments, greater than 75% (v/v) of neutral polysaccharides are in the first supernatant and less than 25% (v/v) of neutral polysaccharides are in the first precipitate. In some embodiments, greater than 80% (v/v) of neutral polysaccharides are in the first supernatant and less than 20% (v/v) of neutral polysaccharides are in the first precipitate. In some embodiments, greater than 85% (v/v) of neutral polysaccharides are in the first supernatant and less than 15% (v/v) of neutral polysaccharides are in the first precipitate.

In some embodiments, greater than 90% (v/v) of neutral polysaccharides are in the first supernatant and less than 10% (v/v) of neutral polysaccharides are in the first precipitate. In some embodiments, greater than 95% (v/v) of neutral polysaccharides are in the first supernatant and less than 5% (v/v) of neutral polysaccharides are in the first precipitate. In some embodiments, greater than 96% (v/v) of neutral polysaccharides are in the first supernatant and less than 4% (v/v) of neutral polysaccharides are in the first precipitate. In some embodiments, greater than 97% (v/v) of neutral polysaccharides are in the first supernatant and less than 3% (v/v) of neutral polysaccharides are in the first precipitate. In some embodiments, greater than 98% (v/v) of neutral polysaccharides are in the first supernatant and less than 2% (v/v) of neutral polysaccharides are in the first precipitate. In some embodiments, greater than 99% (v/v) of neutral polysaccharides are in the first supernatant and less than 1% (v/v) of neutral polysaccharides are in the first precipitate.

In some embodiments, the present method advantageously provides a high percent yield of polysaccharides from the cell lysate. "Percent yield" or "percent recovery" refers to the amount of polysaccharide isolated after purification, relative to the total amount of polysaccharide present in the cell lysate prior to purification. In some embodiments, the percent yield of polysaccharides in the retentate, the second supernatant, and/or the concentrated polysaccharide is greater than 50% relative to the polysaccharides in the cell lysate. In some embodiments, the percent yield of polysaccharides in the retentate, the second supernatant, and/or the concentrated polysaccharide is greater than 50% relative to the polysaccharides in the cell lysate. In some embodiments, the percent yield of polysaccharides in the retentate, the second supernatant, and/or the concentrated polysaccharide is greater than 55% relative to the polysaccharides in the cell lysate. In some embodiments, the percent yield of polysaccharides in the retentate, the second supernatant, and/or the concentrated polysaccharide is greater than 60% relative to the polysaccharides in the cell lysate. In some embodiments, the percent yield of polysaccharides in the retentate, the second supernatant, and/or the concentrated polysaccharide is greater than 65% relative to the polysaccharides in the cell lysate.

In some embodiments, the percent yield of polysaccharides in the retentate, the second supernatant, and/or the concentrated polysaccharide is greater than 70% relative to the polysaccharides in the cell lysate. In some embodiments, the percent yield of polysaccharides in the retentate, the second supernatant, and/or the concentrated polysaccharide is greater than 75% relative to the polysaccharides in the cell lysate. In some embodiments, the percent yield of polysaccharides in the retentate, the second supernatant, and/or the concentrated polysaccharide is greater than 80% relative to the polysaccharides in the cell lysate. In some embodiments, the percent yield of polysaccharides in the retentate, the second supernatant, and/or the concentrated polysaccharide is greater than 85% relative to the polysaccharides in the cell lysate. In some embodiments, the percent yield of polysaccharides in the retentate, the second supernatant, and/or the concentrated polysaccharide is greater than 90% relative to the polysaccharides in the cell lysate. In some embodiments, the percent yield of polysaccharides in the retentate, the second supernatant, and/or the concentrated polysaccharide is greater than 95% relative to the polysaccharides in the cell lysate. In some embodiments, the percent yield of polysaccharides in the retentate, the second supernatant, and/or the concentrated polysaccharide is 35% to 80% relative to the polysaccharides in the cell lysate. In some embodiments, the polysaccharides in the retentate, the second supernatant, and/or the concentrated polysaccharide comprise positively charged polysaccharides, neutral polysaccharides, negatively charged polysaccharides, or combination thereof.

In some embodiments, the present disclosure provides a composition comprising a cell lysate described herein, and a neutralization solution described herein. In some embodiments, the present disclosure provides a composition comprising a cell lysate described herein, and a precipitation solution described herein. In some embodiments, the cell lysate is derived from a bacterial cell or a fungal cell. In some embodiments, the neutralization solution comprises NaCl. In some embodiments, the precipitation solution comprises CTAB. In some embodiments, the present disclosure provides a composition comprising a precipitate and a supernatant, wherein the precipitate comprises an impurity described herein, and the supernatant comprises a polysaccharide described herein. In some embodiments, the impurity comprises a polynucleotide, e.g., DNA, a protein, or combination thereof. In some embodiments, the supernatant comprises: a positively charged polysaccharide, a neutral polysaccharide, a negatively charged polysaccharide, or combination thereof; NaCl; and CTAB.

In some embodiments, the present disclosure provides a second composition comprising a second precipitate and a second supernatant, wherein the second precipitate comprises CTAB and the second supernatant comprises a polysaccharide described herein. In some embodiments, the second supernatant comprises: a positively charged polysaccharide, a neutral polysaccharide, a negatively charged polysaccharide, or combination thereof; NaCl; and KI.

In some embodiments, the present disclosure provides a method of making a polysaccharide vaccine, the method comprising purifying a polysaccharide from a cell lysate, wherein the purifying comprises (a) partially purifying the cell lysate comprising a polysaccharide and an impurity to obtain a clarified crude lysate; (b) mixing the clarified crude lysate with a neutralization solution comprising about 100 mM to about 2 M salt to form a neutralized lysate; (c) mixing the neutralized lysate with a precipitation solution comprising about 0.1% v/v to about 6% v/v cetyltrimethylammonium bromide (CTAB) to form a first supernatant and a first precipitate; and (d) separating the first precipitate from the first supernatant, wherein the polysaccharide is substantially located in the first supernatant.

In some embodiments, the polysaccharide comprises chitosan, glucan, mannose, inulin, galactose, galacturonic acid, 2-acetamido-4-amino-2,4,6-trideoxygalactose (AATGalp), glucuronic acid, glucose, rhamnose, N-acetylmannosamine (ManNAc), N-acetyl-L-fucosamine (FucNAc), beta-galactofuranose (beta-Galf), or combination thereof. In some embodiments, the polysaccharide is further conjugated with a protein or polypeptide. Methods of conjugating polysaccharides to proteins or polypeptides are known in the art and are described in, e.g., Guo et al., Methods Mol Med 66: 49-54 (2001), Turner et al., Syn Sys Biol 2(1): 49-58 (2017), and US Patent Publication No. 2007/0141084.

In some embodiments, the protein or polypeptide is derived from the same cell as the polysaccharide. In some embodiments, the protein or polypeptide is derived from the same organism as the polysaccharide. In some embodiments, the protein or polypeptide is derived from a different organism as the polysaccharide. In some embodiments, the organism is a bacterial organism. In some embodiments, the organism is a fungal organism. In some embodiments, the protein or polypeptide generates an immune response in a host cell of the organism from which the protein or polypeptide is derived. In some embodiments, the protein or polypeptide is a vaccine antigen.

In some embodiments, the present disclosure provides a vaccine comprising a polysaccharide purified by a method provided herein. In some embodiments, the polysaccharide is an adjuvant of the vaccine. In some embodiments, the polysaccharide is an antigen of the vaccine. In some embodiments, the vaccine comprises the polysaccharide conjugated to a different antigen. In some embodiments, the polysaccharide is conjugated to a protein or polypeptide as described herein, e.g., a protein or polypeptide vaccine antigen. In some embodiments, a polysaccharide conjugated to a protein or polypeptide generates a stronger immune response from a host cell compared with an immune response to the polysaccharide or the protein or polypeptide alone, thereby providing improved protection to the host cell against the organism. In some embodiments, a vaccine comprising a polysaccharide provided herein provides improved protection to the host cell against the organism compared with a vaccine that does not comprise the polysaccharide. In some embodiments, a vaccine comprising a polysaccharide vaccine adjuvant provided herein provides improved protection to the host cell against the organism compared with a vaccine that does not comprise the polysaccharide vaccine adjuvant. In some embodiments, the polysaccharide comprises chitosan, glucan, mannose, inulin, galactose, galacturonic acid, 2-acetamido-4-amino-2,4,6-trideoxygalactose (AATGalp), glucuronic acid, glucose, rhamnose, N-acetylmannosamine (ManNAc), N-acetyl-L-fucosamine (FucNAc), beta-galactofuranose (beta-Galf), or combination thereof. Non-limiting examples of polysaccharide vaccines include: PREVNAR 13®, MENINGITEC®, and NEISVAC-C® from Pfizer/Baxter International; and MENVEO® and MENJUGATE® from GlaxoSmithKlin).

In some embodiments, the present disclosure provides a delivery system comprising a polysaccharide purified by a method provided herein. As used herein, a "delivery system" refers to a formulation and/or device that enables and/or facilitates the introduction of a substance, e.g., into the body. In some embodiments, the delivery system delivers a therapeutic substance into the body. In some embodiments, the delivery system delivers a cosmetic-enhancement substance into the body. In some embodiments, the delivery system delivers a biomolecule into the body, e.g., a polynucleotide, a protein or peptide, a lipid, a small molecule, or combination thereof. In some embodiments, the delivery system delivers a polynucleotide for gene therapy. In some embodiments, the delivery system delivers a therapeutic RNA. In some embodiments, the delivery system delivers a therapeutic protein or peptide. In some embodiments, the delivery system delivers an antibody or fragment thereof. In some embodiments, the delivery system delivers a liposome. In some embodiments, the delivery system delivers an anticancer drug. In some embodiments, the delivery system delivers an antimicrobial agent. In some embodiments, the delivery system delivers a wound healing agent. In some embodiments, the polysaccharide comprises pullulan, hyaluronic acid, alginate, chitosan, dextran, cellulose, or combination thereof. In some embodiments, the delivery system is a drug capsule, e.g., PLANTCAPS® (Capsugel). In some embodiments, the delivery system is a dermal filler, e.g., JUVEDERM® (Allergan).

In some embodiments, the present disclosure provides a pharmaceutical composition comprising a polysaccharide purified by a method provided herein. In some embodiments, the pharmaceutical composition comprises a polysaccharide having antimicrobial activity. For example, sulfated polysaccharides from marine algae may have antimicrobial and anti-biofilm activities, e.g., against dental plaque bacteria, as well as antioxidant, anticoagulant, and immunostimulant activity. See, e.g., Barahona et al., *Bioactive Carbohydrates and Dietary Fibre* 4(2):125-138, 2014; and Xu et al., *Marine Drugs* 15(12):388, 2017. In some embodiments, the polysaccharide comprises chitosan. In a further example, polysaccharides from lactic acid bacteria, e.g., from the *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus*, and *Weissella* genera, may have beneficial antitumor activity, anti-atherosclerotic effect, immunomodulation activity, and prebiotic effect. See, e.g., Lynch et al., *Ann Rev Food Sci Technol* 9:155-176, 2018. In some embodiments, the pharmaceutical composition comprises a polysaccharide from marine algae. In some embodiments, the pharmaceutical composition comprises a polysaccharide from lactic acid bacteria.

In some embodiments, the present disclosure provides a polysaccharide purified by a method provided herein. In some embodiments, the polysaccharide is used in a vaccine as described herein. In some embodiments, the polysaccharide is used as a vaccine adjuvant. In some embodiments, the polysaccharide is further conjugated to a protein or polypeptide as described herein, e.g., a protein or polypeptide vaccine antigen. In some embodiments, the polysaccharide is used in a drug delivery system as described herein. In some embodiments, the polysaccharide is used in a pharmaceutical composition as described herein.

All references cited herein, including patents, patent applications, papers, textbooks and the like, and the references cited therein, to the extent that they are not already, are hereby incorporated herein by reference in their entirety.

EXAMPLES

Example 1

The following procedure was tested to isolate polysaccharides from Streptococcus cells of two different serotypes (serotype 3 and 4).

1) Precipitation of DNA using CTAB and NaCl;
2) Depth filtration to remove precipitate;
3) Precipitation with KI to remove CTAB;
4) Centrifugation to remove precipitate;
5) Carbon filtration to remove proteins and other impurities;
6) Ceramic hydroxyapatite type (CHT) column chromatography coupled with a SARTOBIND phenyl membrane chromatography to further remove impurities;
7) Tangential flow filtration for polysaccharide concentration.

The reference cells were subjected to a solution with CTAB and no NaCl. The test cells were subjected to a solution with CTAB and 400 mM NaCl.

Overall polysaccharide yields are described in Table 1:

TABLE 1

| | Yield | |
|---|---|---|
| Serotype | No NaCl (reference solution) | 400 mM NaCl (test solution) |
| Serotype 3 | 43% | 52% |
| Serotype 4 | 61% | 78% |

As shown in Table 1, cells contacted with solutions containing NaCl led to 9% increase in polysaccharide yield (from 43% to 52%) in *Streptococcus* serotype 3 cells, and a 17% increase in polysaccharide yield (from 61% to 78%) in *Streptococcus* serotype 4 cells.

Exemplary CTAB concentrations from step 1 are listed in Table 2. Further suitable salts and their concentrations are listed in Table 3.

TABLE 2

| CTAB Concentrations CTAB Concentration (w/v) |
|---|
| 0.1% |
| 0.2% |
| 0.3% |
| 0.4% |
| 0.5% |
| 0.6% |
| 0.7% |
| 0.8% |
| 0.9% |
| 1% |
| 2% |
| 3% |
| 4% |
| 5% |
| 6% |

TABLE 3

| Salts | |
|---|---|
| Salt | Concentration |
| NaCl | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |

TABLE 3-continued

| Salts | |
| --- | --- |
| Salt | Concentration |
| KCl | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |
| CH$_4$Cl | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |
| NH$_4$Cl | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |
| MgCl$_2$ | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |
| CaCl$_2$ | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |
| Na$_3$PO$_4$ | 100 mM |
| | 200 mM |
| | 300 mM |
| | 400 mM |
| | 500 mM |
| | 600 mM |
| | 700 mM |
| | 800 mM |
| | 900 mM |
| | 1 M |
| | 2 M |

Example 2

The following procedure is used to isolate polysaccharides, e.g., positively charged, negatively charged, and/or neutral polysaccharides (such as pullulan), from *Aureobasidium pullulans* cells. The cells are *A. pullulans* var. *pullulans*. *A. pullulans* var. melanogenicum, or both. The cells contain one or more of A. pullulans strain MC 571, strain MC 573, strain MC 574, strain MC 576, strain MC 711, strain MC 737, strain MC 745, strain MC 767, strain CBS 701.76, and strain CBS 105.22

1) Precipitation of DNA using CTAB and salt;
2) Depth filtration to remove precipitate;
3) Precipitation with KI to remove CTAB;
4) Centrifugation to remove precipitate;
5) Carbon filtration to remove proteins and other impurities;
6) Ceramic hydroxyapatite type (CHT) column chromatography coupled with a SARTOBIND phenyl membrane chromatography to further remove impurities;
7) Tangential flow filtration for polysaccharide concentration.

The concentrations of CTAB used in the procedure are provided in Table 2. The concentrations and types of salt used in the procedure are provided in Table 3.

Example 3

The procedure described in Example 2 is used to isolate polysaccharides, e.g., positively charged, negatively charged, and/or neutral polysaccharides, from *Staphylococcus aureus* cells. The cells contain one or more of *S. aureus* serotypes 1, 2, 5, 8, 336, or NT. The concentrations of CTAB used in the procedure are provided in Table 2. The concentrations and types of salt used in the procedure are provided in Table 3.

Example 4

The procedure described in Example 2 is used to isolate polysaccharides, e.g., positively charged, negatively charged, and/or neutral polysaccharides, from *Salmonella enterica* cells. The cells contain one or more of *S. enterica* serotypes *Typhi, Typhimurium, Choleraesuis, Schwarzengrund, Derby, Haifa, Stanley, Newport, Virchow, Paratyphi, Singapore, Agona, Panama, Blockley, Anatum, Infantis, Enteritidis, Heidelberg, Muenchen, Javiana, Montevideo, Thompson, or Oranienburg. The concentrations of CTAB used in the procedure are provided in Table* 2. The concentrations and types of salt used in the procedure are provided in Table 3.

Example 5

The procedure described in Example 2 is used to isolate polysaccharides, e.g., positively charged, negatively charged, and/or neutral polysaccharides, from *Neisseria meningitidis* cells.

The cells contain one or more of *N. meningitidis* serotypes A, B, C, W, or Y. The concentrations of CTAB used in the procedure are provided in Table 2. The concentrations and types of salt used in the procedure are provided in Table 3.

Example 6

The procedure described in Example 2 is used to isolate polysaccharides, e.g., positively charged, negatively charged, and/or neutral polysaccharides, from *Mycobacterium tuberculosis* cells. The cells contain one or more of *M. tuberculosis* serotypes 4, 8, 9, or NT. The concentrations of CTAB used in the procedure are provided in Table 2. The concentrations and types of salt used in the procedure are provided in Table 3.

Example 7

The procedure described in Example 2 is used to isolate polysaccharides, e.g., positively charged, negatively charged, and/or neutral polysaccharides, from *Aspergillus fumigatus* cells. The concentrations of CTAB used in the procedure are provided in Table 2. The concentrations and types of salt used in the procedure are provided in Table 3.

Example 8

The procedure described in Example 2 is used to isolate polysaccharides, e.g., positively charged, negatively charged, and/or neutral polysaccharides, from *Candida albicans* cells. The cells contain one or more of *C. albicans* serotypes A or B. The concentrations of CTAB used in the procedure are provided in Table 2. The concentrations and types of salt used in the procedure are provided in Table 3.

Example 9

The procedure described in Example 2 is used to isolate polysaccharides, e.g., positively charged, negatively charged, and/or neutral polysaccharides, from *Cryptococcus neoformans* cells. The cells contain one or more of *C. neoformans* serotypes A, D, or AD hybrid. The concentrations of CTAB used in the procedure are provided in Table 2. The concentrations and types of salt used in the procedure are provided in Table 3.

Example 10

The procedure described in Example 2 is used to isolate polysaccharides, e.g., positively charged, negatively charged, and/or neutral polysaccharides, from *Histoplasma capsulatum* cells. The cells contain one or more of *H. capsulatum* serotypes 1, 2, 3, 4, or 5. The concentrations of CTAB used in the procedure are provided in Table 2. The concentrations and types of salt used in the procedure are provided in Table 3.

What is claimed is:

1. A method of purifying polysaccharides from a cell lysate, the method comprising
  a. partially purifying the cell lysate comprising a polysaccharide and an impurity to obtain a clarified crude lysate;
  b. mixing the clarified crude lysate with a neutralization solution to form a neutralized lysate comprising about 100 mM to about 2 M salt;
  c. mixing the neutralized lysate with a precipitation solution comprising cetyltrimethylammonium bromide (CTAB) to form a first supernatant and a first precipitate, wherein the first supernatant comprises about 0.5% v/v to about 4% v/v CTAB; and
  d. separating the first precipitate from the first supernatant,
  wherein the polysaccharide is substantially located in the first supernatant; and
  wherein the method is capable of purifying positively charged, negatively charged, and neutral polysaccharides, and wherein the positively charged, negatively charged, and neutral polysaccharides are substantially located in the first supernatant.

2. The method of claim 1, wherein the partially purifying the cell lysate comprises precipitation, centrifugation, filtration, or combination thereof.

3. The method of claim 2, wherein the filtration comprises depth filtration, tangential flow filtration (TFF), sterile filtration, or combination thereof.

4. The method of claim 1, wherein:
  the neutralized lysate comprises about 200 mM to about 1 M salt; and/or
  the salt is NaCl, KCl, $CH_4Cl$, $NH_4Cl$, $MgCl_2$, $CaCl_2$, $Na_3PO_4$, or combination thereof.

5. The method of claim 1, wherein the mixing of the clarified crude lysate with the neutralization solution in (b) is performed simultaneously with or prior to a filtration step, wherein the filtration step is prior to (c).

6. The method of claim 1, wherein the cell lysate comprises a positively charged polysaccharide, a neutral polysaccharide, a negatively charged polysaccharide, or combination thereof, wherein the positively charged polysaccharide, the neutral polysaccharide, the negatively charged polysaccharide, or combination thereof are substantially in the first supernatant, and wherein the impurity is substantially in the first precipitate.

7. The method of claim 1, wherein the impurity comprises a polynucleotide.

8. The method of claim 1, wherein the mixing in (b), (c), or both, is performed by shaking, stirring, or pumping; and/or wherein the separating in (d) is performed by centrifugation, filtration, or combination thereof.

9. The method of claim 1, further comprising subjecting the first supernatant to ultrafiltration, diafiltration, or combination thereof to produce a retentate and a permeate, wherein the polysaccharide is substantially in the retentate, and the CTAB is substantially in the permeate.

10. The method of claim 9, further comprising subjecting the retentate to carbon filtration, chromatography, or combination thereof.

11. The method of claim 1, further comprising adding potassium iodide (KI) to the first supernatant to form a second precipitate and a second supernatant, wherein the polysaccharide is substantially in the second supernatant and the CTAB is substantially in the second precipitate.

12. The method of claim 11, wherein the second supernatant comprises the KI and further comprises NaCl.

13. The method of claim 11, wherein the method does not comprise a chromatography step prior to the adding of KI.

14. The method of claim 11, further comprising separating the second supernatant from the second precipitate by centrifugation, filtration, or combination thereof; and subjecting the second supernatant to carbon filtration, chromatography, or combination thereof.

15. The method of claim 14, further comprising performing ultrafiltration, diafiltration, or combination thereof following the chromatography, to concentrate the polysaccharide.

16. The method of claim 1, wherein the method comprises at least one of:
  (i) the method does not comprise a first precipitate containing greater than 10% of the polysaccharides in the cell lysate during the purification;
  (ii) the positively charged polysaccharide, the neutral polysaccharide, the negatively charged polysaccharide, or the combination thereof are not substantially precipitated during the purification;
  (iii) the positively charged polysaccharide, the neutral polysaccharide, the negatively charged polysaccharide, or the combination thereof are not isolated from each other;

(iv) greater than 90% (v/v) of negatively charged poly-
saccharides are in the first supernatant and less than
10% (v/v) of negatively charged polysaccharides are in
the first precipitate;

(v) the percent yield of polysaccharides is greater than
30% relative to the polysaccharides in the cell lysate.

17. The method of claim 1, wherein the cell lysate is
derived from a bacterial cell or a fungal cell.

18. The method of claim 17, wherein the cell is a
*Streptococcus* cell of serotype 1, 2, 3, 4, 5, 6A, 6B, 7F, 8, 9N,
9V, 10A, 11A, 12F, 14, 15A, 15B, 17F, 18C, 19A, 19F, 20A,
22F, 23F, or 33F.

19. The method of claim 17, wherein the cell lysate is
derived from a *Staphylococcus* cell, *Streptococcus* cell,
*Salmonella* cell, *Neisseria* cell, *Mycobacterium* cell, or
*Aureobasidium* cell.

20. A method of purifying polysaccharides from a cell
lysate, the method comprising a. partially purifying the cell lysate comprising an impu-
rity and a polysaccharide to obtain a clarified crude
lysate;

b. mixing the clarified crude lysate with a neutralization
solution to form a neutralized lysate comprising about
400 mM sodium chloride (NaCl);

c. mixing the neutralized lysate with cetyltrimethylam-
monium bromide (CTAB) to form a first supernatant and a first precipitate, wherein the first supernatant
comprises about 1.0% v/v CTAB;

d. separating the first precipitate from the first superna-
tant;

e. mixing the first supernatant with potassium iodide (KI)
to form a second precipitate and a second supernatant;
and f. separating the second precipitate from the second
supernatant, wherein the polysaccharide is substantially located in the
second supernatant; and wherein the method is capable of purifying positively
charged, negatively charged, and neutral polysaccha-
rides, and wherein the positively charged, negatively
charged, and neutral polysaccharides are substantially
located in the first supernatant.

21. A method of making a polysaccharide vaccine, the
method comprising purifying a polysaccharide according to
the method of claim 1 to obtain the polysaccharide vaccine.

22. The method of claim 21, wherein the polysaccharide
comprises chitosan, glucan, mannose, inulin, galactose,
galacturonic acid, 2-acetamido-4-amino-2,4,6-trideoxyga-
lactose (AATGalp), glucuronic acid, glucose, rhamnose,
N-acetylmannosamine (ManNAc), N-acetyl-L-fucosamine
(FucNAc), beta-galactofuranose (beta-Galf), or combination
thereof.

* * * * *